United States Patent [19]

Yamatsu et al.

[11] 4,382,151
[45] May 3, 1983

[54] 6,10,14,18-TETRAMETHYL-5,9,13,17-NONADECATETRAENE-2-OL

[75] Inventors: Isao Yamatsu, Kawaguchi; Yuichi Inai; Shinya Abe, both of Tokyo; Takeshi Suzuki, Abiko; Toshiharu Ohgoh, Kounan; Manabu Murakami, Kakamigahara; Kiyoshi Oketani; Hideaki Fujisaki, both of Takehayamachi, all of Japan

[73] Assignee: Eisai Co., Ltd., Tokyo, Japan

[21] Appl. No.: 296,728

[22] Filed: Aug. 27, 1981

[30] Foreign Application Priority Data

Aug. 29, 1980 [JP] Japan .................. 55-118452

[51] Int. Cl.$^3$ .................................... C07L 33/02
[52] U.S. Cl. .................... 568/875; 424/343; 568/857
[58] Field of Search ............. 568/880, 878, 876, 875, 568/845, 857; 424/343

[56] References Cited

U.S. PATENT DOCUMENTS

| 3,939,202 | 2/1976 | Matsui et al. | 568/875 |
| 3,980,718 | 9/1976 | Shabaai et al. | 568/875 |
| 4,006,193 | 2/1977 | Ninagawa et al. | 568/875 |
| 4,073,813 | 9/1977 | Cordier | 568/881 |
| 4,292,452 | 9/1981 | Lee et al. | 568/875 |

FOREIGN PATENT DOCUMENTS 2216263 12/1974 France .................. 568/881

OTHER PUBLICATIONS

Tschesche, "Chemical Abstracts", vol. 81, (1974), 12809.

Matsui et al., "Chemical Abstracts", vol. 84, (1976), 84:44468x.

*Primary Examiner*—Werren B. Lone
*Attorney, Agent, or Firm*—Flynn, Thiel, Boutell & Tanis

[57] ABSTRACT

6,10,14,18-Tetramethyl-5,9,13,17-nonadecatetraene-2-ols of the general formula:

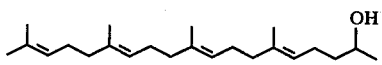

3 Claims, No Drawings

6,10,14,18-TETRAMETHYL-5,9,13,17-NONADECATETRAENE-2-OL

The present invention relates to new compounds, i.e. 6,10,14,18-tetramethyl-5,9,13,17-nonadecatetraene-2-ols of the general formula:

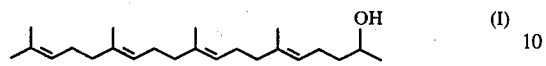

as well as a process for producing the same and an anti-ulcer agent comprising the same.

In the specification of Japanese Patent Laid-Open No. 145,922/1978, it is disclosed that 6,10,14,18-tetramethyl-5,9,13,17-nonadecatetraene-2-one of the general formula:

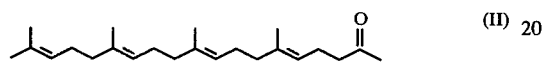

has an anti-ulcer effect. It has been found that when said compound is administered to animals, compound of the present invention represented by above general formula (I) is formed by the metabolism. After investigations wherein the compounds of the present invention were synthesized and pharmacological effects thereof were examined, it has been found that the above compounds have a strong anti-ulcer effect.

The compounds of the present invention can be produced by reducing compounds of above general formula (II). As the reducing agent, a compound which reduces a ketone into an alcohol but which is inert to the double bond of the isoprene chain is selected. As such reducing agents, there may be mentioned, for example, sodium borohydride and lithium aluminum hydride. As the solvent, an alcoholic solvent such as methanol or ethanol is preferred. Compounds of general formula (II) used as the starting material may be obtained by a process shown in the specification of Japanese Patent Laid-Open No. 145,922/1978.

The results of the pharmacological tests of the compounds of the present invention will be shown below.

Effects on the cold-restraint stress ulcer

10 Female SD rats each weighing 160–200 g were placed in a wire net restraining cage and allowed to stand in a low temperature room at 4° C. for two hours. Then, the rats were sacrificed and their stomachs were taken out. Each stomach was inflated with about 10 ml. of isotonic sodium chloride solution and then immersed in 5% neutral formalin solution for about five minutes according to a method of Brodie et al. [Gastroenterology, 38, 354–360 (1960)]. Thereafter, the stomach was incised and a length of each ulcer caused in the glandular part of the stomach was measured. The sum of the lengths thereof was taken as an ulcer index.

200 mg/Kg of the compound of the present invention was administered orally by means of a gastric tube 30 minutes before the application of the stress. The compound of the present invention was given in the form of an emulsion prepared by adding one drop of polyoxyethylene sorbitan monooleate to a solution of the compound in 5% gum arabic solution so as to control the dose to 0.5 ml./100 g B.W.

As a control, 6,10,14,18-tetramethyl-5,9,13,17-nonadecatetraene-2-on of above general formula (II) was employed and subjected to the same test as above. Further, a blank test was carried out wherein gum arabic-polyoxyethylenesorbitan monooleate emulsion alone was administered.

From the ulcer index obtained as above, ulcer inhibition rates were calculated as follows:

Inhibition rate (%) = 100 × [(Ulcer index in the blank test)-(Ulcer index of the test compound)] ÷ (Ulcer index in the blank test).

TABLE 1

| Test compound | Inhibition rate (%) |
| --- | --- |
| Compound of the present invention (6,10,14,18-Tetramethyl-5,9,13,17-nonadecatetraene-2-ol) | 86.8 |
| Control compound (6,10,14,18-Tetramethyl-5.9.13.17-nonadecatetraene-2-on) | 76.1 |

Toxicity tests 5,000 mg/Kg of the compound of the present invention was administered to 6 female SD rats each weighing 160–200 g. There was observed no case of death.

The results of the above pharmacological tests suggest that the compound of the present invention is an excellent antiulcer agent. It may be used for the treatment and prevention of a gastric ulcer, duodenal ulcer or the like. The compound of the present invention is administered generally in a dosage of 50–2,000 mg/day for adults internally or externally. The compound may be administered in the form of powders, granules, hard capsules, tablets, soft elastic capsules, injections, etc. Those pharmaceutical preparations can be prepared using an ordinary carrier for the pharmaceutical preparations in a usual manner.

The following examples further illustrate the present invention.

EXAMPLE 1

Synthesis of 6,10,14,18-tetramethyl-5,9,13,17-nonadecatetraene-2-ol 1 g of 6,10,14,18-tetramethyl-5,9,13,17-nonadecatetraene-2-on was dissolved in 20 ml. of methanol. 60 mg of sodium borohydride was added to the solution and the whole was stirred for 30 minutes. The reaction liquid was poured in ice-water. Dilute hydrochloric acid solution was added thereto to make the same acidic. The liquid was then subjected to the extraction with 50 ml. of n-hexane. The extract was washed with water and dried with magnesium sulfate. The solvent was distilled out to obtain 1 g of an oily product. The product was purified according to silica gel column chromatography to obtain 0.95 g of the intended product in the form of a colorless oil from 10% ether/n-hexane effluent.

Mass spectrum (m/e): 332 (M+)

Elementary analysis as $C_{23}H_{40}O$:

| | C | H |
| --- | --- | --- |
| Theoretical: | 83.06 | 12.13 |
| Found: | 83.12 | 12.09 |

NMR Spectrum ($\delta$, $CDCl_3$): 1.16 (3H, d, J=7 Hz), 1.58 (9H, s), 1.65 (6H, s), 1.2–1.6 (2H, 1.8–2.3 (15H), 3.74 (1H, t, q, J=6 Hz, 6 Hz), 5.04 (4H, m).

The embodiments of the invention in which an exclusive property or privilege is claimed are defined as follows:

1. 6,10,14,18-Tetramethyl-5,9,13,17-nonadecatetraene-2-ols of the formula:

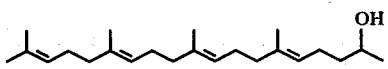

2. An anti-ulcer agent comprising a therapeutically effective amount of 6,10,14,18-tetramethyl-5,9,13,17-nonadecatetraene-2-ol of the formula:

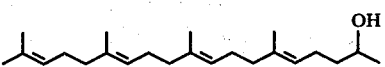

and a pharmaceutically acceptable carrier.

3. A method of treating ulcers or preventing the occurrence of ulcers, which comprises administering to a patient requiring such treatment a therapeutically effective amount of 6,10,14,18-tetramethyl-5,9,13,17-nonadecatetraene-2-ol of the formula

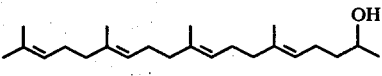

in combination with a pharmaceutically acceptable carrier.

* * * * *